United States Patent [19]

Rower

[11] Patent Number: 5,735,301
[45] Date of Patent: Apr. 7, 1998

[54] UROSTOMY PATIENT EQUIPMENT IRRIGATION SYSTEM

[76] Inventor: Gary Rower, 105 White Oak Trail, Peachtree City, Ga. 30269

[21] Appl. No.: 605,670

[22] Filed: Feb. 22, 1996

[51] Int. Cl.$^6$ ..................................... B08B 9/08
[52] U.S. Cl. ............... 134/167 R; 134/166 C; 134/102.1; 134/166 R; 604/334; 604/277
[58] Field of Search .................. 134/116 C, 169 C, 134/168 C, 99.2, 102.1, 100.1, 166 R, 167 R, 169 R; 239/310, 318; 604/332, 334, 277

[56] References Cited

U.S. PATENT DOCUMENTS

| | | |
|---|---|---|
| D. 99,136 | 3/1936 | Newman . |
| D. 211,563 | 7/1968 | Cherry . |
| 1,416,347 | 5/1922 | Gregory . |
| 2,215,132 | 9/1940 | Parker . |
| 2,724,583 | 11/1955 | Targosh et al. . |
| 3,776,468 | 12/1973 | Davenport . |
| 3,825,187 | 7/1974 | Tatge ............................ 239/318 |
| 3,829,023 | 8/1974 | Bouollard et al. ............. 239/318 |
| 4,029,260 | 6/1977 | Herrick ......................... 134/100.1 |
| 4,058,259 | 11/1977 | Schantz ........................ 239/318 |
| 4,527,740 | 7/1985 | Gunzel, Jr. et al. ........... 239/318 |
| 4,586,927 | 5/1986 | Jensen ........................... 604/334 |
| 4,654,037 | 3/1987 | Fenton .......................... 604/277 |
| 4,969,603 | 11/1990 | Norman ........................ 239/318 |
| 5,096,503 | 3/1992 | Wellman . |
| 5,330,447 | 7/1994 | Barht ............................ 604/277 |
| 5,419,495 | 5/1995 | Berfield . |
| 5,470,325 | 11/1995 | Fundock ....................... 604/334 |
| 5,503,633 | 4/1996 | Saunders et al. ............. 604/334 |
| 5,529,244 | 6/1996 | Horvath, Jr. et al. ......... 239/134 |

FOREIGN PATENT DOCUMENTS

| | | | |
|---|---|---|---|
| 1184822 | 4/1985 | Canada .................... 604/334 |
| 2511815 | 9/1975 | Germany ................. 604/334 |
| 2600079 | 7/1976 | Germany ................. 239/318 |
| 80033598 | 1/1982 | Netherlands ............. 239/318 |
| 1195251 | 6/1970 | United Kingdom ..... 134/100.1 |

OTHER PUBLICATIONS

WO91/17729 604/223 Nov. 1991.

*Primary Examiner*—Frankie L. Stinson
*Attorney, Agent, or Firm*—Randy W. Lacasse

[57] ABSTRACT

A system using a secondary cleansing fluid achieves a fully functional irrigation and cleansing system for a urostomy patient night drainage container and associated tubing and adapter. A connection to a standard interior faucet using pressurized water in conjunction with a negative pressure device creates siphoning of a secondary fluid into fluid contact with the water for mixing. In addition, the system provides for an efficient connection for the night container tubing of less than half an inch in diameter for filling, cleansing, and flushing.

16 Claims, 2 Drawing Sheets

UROSTOMY PATIENT EQUIPMENT IRRIGATION SYSTEM

BACKGROUND OF THE INVENTION

1. Field of Invention

This invention relates, in general, to cleaning surgical bags and tubing, nasal-gastric tubes, colostomy bags and tubing and more specifically to urostomy bags and associated night drainage containers.

Cleansing and deodorizing night drainage containers and connected urostomy pouches is often difficult for the users of such devices. The difficulty presents itself during manipulation, filling and flushing of the night container using its adapter, tubing and drain. Urostomy tubing has an internal crossection that is typically less than one-half inch in diameter, making cleansing not an easy task.

The prior art has failed to provide for an efficient means of irrigation, cleansing, and deodorizing the night container for the urostomy bags system.

2. Discussion of Prior Art

In order to provide background information so that the invention may be completely understood and appreciated in its proper context, reference may be made to a number of prior art patents as follows:

U.S. Pat. No. 5,096,503 to Wellman is concerned with an apparatus for cleaning body waste bags with water through the use of a faucet diverter valve. This patent proposes a diverter valve with internally threaded attachment to the faucet for diverting water from normal faucet flow to channel the flow through a reduced size opening attached to the connect outlet tube of the waste bag, thereby providing a means of washing the bag with water. This patent does not address the irrigation with any other cleansing or deodorizing fluid except faucet water under its associated pressure. The present invention assists in cleansing the night urostomy container with a mixture of water and a secondary cleansing fluid by means of a negative pressure action on the secondary fluid provided by the pressurized water.

U.S. Pat. No. 5,419,495 to Berfield provides for an auxiliary chemical intake system for a pressure washer having a spray nozzle in fluid communication with a pressurized water source and either an internal or external fluid tank or both tanks. This patent provides a complex apparatus by which the fluid agent in the external tank may be a different fluid and its rate of introduction into the water stream is variable under the control of several variable diameter apertures. This patent does not provide for the rapid easy attachment of the device to a standard interior faucet water supply, nor for the attachment of small diameter tubing required to flush the night urostomy containers. The patent also lacks a fluid container designed to minimize the cleaning/deodorizing fluid waste and reduce the possibility of accidental spillage. The patent requires fluid flow rates and pressures to operate that far exceed those feasible with the urostomy bag and tubing. Operating at these pressures and flow rates could cause premature failure of any of the tubing, bag or connections. The present invention distinguishes itself therefrom by using a faucet adapter intake tube for the water intake and an adapter tip at the fluid mixing end of the system to allow for efficient adapting to the tubing of the urostomy night container for cleaning, deodorizing and flushing and providing a container specifically designed for the reduction of cleansing/deodorizing fluid waste and accidental spillage. The simple single fluid internally attachable container of the present invention is in fluid communication with the pressurized water.

U.S. Pat. No. 2,215,132 to Parker discloses methods and apparatus for distributing liquid solutions employing a water jet pump and adapter for connection to an ordinary garden hose with ordinary pressure specifically for liquid fertilizer application to lawns within limits of prescribed concentrations. The liquid fertilizer solution is housed primarily in a stationary pail. This is inadequate for use with urostomy night containers because it is susceptible to spillage and to liquid waste due to settling in the inaccessible regions at the bottom of the pail. The water jet pump device is internally threaded to be secured to the exterior faucet and externally threaded to accept a typical garden hose with a nozzle spray attachment at the terminal end. The patent requires fluid flow rates and pressures to operate that far exceed those feasible with the urostomy bag and tubing. Operating at those pressures and flow rates could cause premature failure of any of the tubing, bag or connections. The present invention distinguishes itself therefrom by using an interior faucet adapter intake tube for the water intake and an adapter tip at the fluid mixing end of the system to allow for efficient adapting to the tubing with a diameter of less than one-half inch connected to the urostomy night container for cleaning, deodorizing and flushing. The present invention also provides an internally attachable cleansing fluid container specifically designed for the reduction of cleansing/deodorizing fluid waste and accidental spillage.

U.S. Pat. No. 2,724,583 to Targosh et al. provides a hose apparatus with liquid mixing nozzle for connection to a primary liquid supply pressure source, such as water, to a secondary liquid which embodied a mixing and discharge nozzle especially designed to mix the liquids and aerate the same in the nozzle for a homogeneous mixture of liquids. The patent requires fluid flow rates and pressures to operate that far exceed those feasible with the urostomy bag and tubing. Operating at those pressures and flow rates could cause premature failure of any of the tubing, bag or connections. The present invention distinguishes itself therefrom by not requiring a complex aspirator mixing valve in the nozzle for aeration and variable homogeneous flow mixing nozzle and by providing an internal container designed to reduce waste and prevent spillage. The present invention further distinguishes itself by having a simple interior faucet adapter intake tube for the water intake and an adapter tip at the fluid mixing end of the system to allow for efficient adapting to the tubing of a diameter, typically less than one half an inch, connected to the urostomy night container for cleaning, deodorizing and flushing.

U.S. Pat. No. 3,776,468 to Davenport provides a spray mix applicator designed particularly for commercial cleaning purposes by the mixing and spraying of a mixture of two liquids at a prescribed flow rate in a prescribed proportion to each other. The system discloses a complicated series of flow-control valve, check flow valve, on-off valve, fittings, couplings and spray tip for connection to an industrial size external drum of secondary fluid. This invention provides a spray mix applicator for threaded attachment to a standard water hose and will spray the mixture of two liquids in a prescribed proportion to each other. The present invention provides for attachment to the interior water supply faucet and a venturi means of providing the suction and fluid mixing effect, coupled with a simple efficient adapter tip for connection to tubing typically less than a half inch in diameter. The present invention also provides a fluid container designed for minimal waste and spill prevention.

U.S. Pat. No. 1,416,347 to Gregory describes a bottle which is of pyramidal three-sided angular design for preventing spillage and having an inner bottom surface in vertical alignment with its mouth and a depression to collect the remainder of fluid when the bottle is nearly empty. The present invention provides a simpler singe stage conical fluid container designed for tip and spillage prevention combined with a simple concave interior bottom surface of the fluid container's base for minimal fluid waste.

U.S. Design Pat. No. 211,563 to Cherry provides for a bottle with a two stage conical design with a single non-threaded lip, approximately one fourth the diameter of the internally convex base. The present inventions' container distinguishes itself by a single stage conical design with a threaded neck whose diameter is, in the preferred embodiment, one half of the diameter of the base with its associated concave internal base.

U.S. Design Pat. No. 99,136 to Newman for an ink bottle with a single stage conical design with a nonthreaded circular neck, approximately one half the diameter of the base, with an internal elliptically concave base that begins approximately one half the height of the bottle. The present invention distinguishes itself by having a secondary fluid container designed with both a threaded neck and a concave internal base that is approximately five sixths the distance from the neck, thereby maximizing the fluid volume of the container while still providing minimal fluid waste.

Whatever the precise merits, features, and advantages of the above cited references, none of them achieves or fulfills the purposes of the urostomy patient equipment irrigation system of the present invention.

SUMMARY OF THE INVENTION

Accordingly, it is a principal object of the present invention to achieve a fully functional irrigation and cleansing system for medical waste containers and in a preferred embodiment, urostomy patient night drainage container and associated tubing and adapter. The disclosed system provides for an efficient connection to a standard interior faucet using pressurized water in conjunction with a negative pressure device to create siphoning of a secondary fluid into fluid contact with the water for mixing. In addition, the present invention provides for an efficient connection for the night container tubing of less than half an inch in diameter for filling, cleansing, and flushing.

It is another principal object of the present invention to provide a container for the deodorizing and cleansing fluid that will minimize fluid waste and be tip and spill resistant while providing a large fluid capacity.

The urostomy patient equipment irrigation system of the present invention overcomes the problems and limitations of cleansing and deodorizing the urostomy night fluid container that is connected to the normal urostomy pouch with an adapter and tubing of less than one half an inch. The night container bag and its associated tubing and adapter require a daily cleaning and flushing with water and a deodorizing fluid. The manual method of filling, flushing and deodorizing the night urostomy container is difficult because of the manipulation required to fill and flush the container using a regular interior water faucet and the night containers' tubing, valve, and drain of less than one-half an inch in diameter.

The present invention provides for a connection to an ordinary interior faucet pressurized water source and for an efficient system for filling, cleansing, and flushing the night container through the tubing and valves of less than one half an inch in diameter.

A system will be described for the suction and fluid mixing of the cleansing deodorizing secondary fluid with a negative pressure device from a container that is designed for minimal waste, easy attachment and detachment, tip and spill resistance, and a large fluid capacity.

The present invention contains the following design elements providing the following features:

a flexible intake tube for a simple, secure, and efficient connection to an ordinary faucet water supply; attachment to a venturi tube providing suction for a secondary cleaning fluid where the venturi tube is in fluid connection with the pressurized primary fluid water to provide mixing with the secondary cleaning fluid; the secondary fluid container threaded cap attached to the venturi tube providing a secure and easy attachment and detachment of the cleansing/deodorizing fluid container; a vent hole in the threaded fluid container cap providing the secondary cleansing fluid at atmospheric pressure; secondary cleansing fluid feed tube attached to the venturi tube at a point providing negative pressure for the suction of the cleansing fluid from the container positioned such that the feed tube lays at the center of the internal concave base for minimal waste of the cleansing fluid; and an adapter tip connected at the distal end of the venturi tube designed for simple, secure, efficient connection to the night urostomy containers' small tubing of less than one half inch in diameter; and a secondary cleansing fluid container designed for easy attachment and detachment, large fluid capacity, and tip and spillage resistance.

The secondary cleansing and deodorizing fluid container is designed with a threaded neck for a secure easy attachment and detachment feature, an internal concave base for minimal waste of the cleansing fluid, a one stage conical design with a base twice the diameter of the top and the internal concave base at approximately five sixth the distance from the top for a large fluid capacity while also providing the tip and spill resistance feature.

DESCRIPTION OF THE PREFERRED EMBODIMENTS

Figure 1:
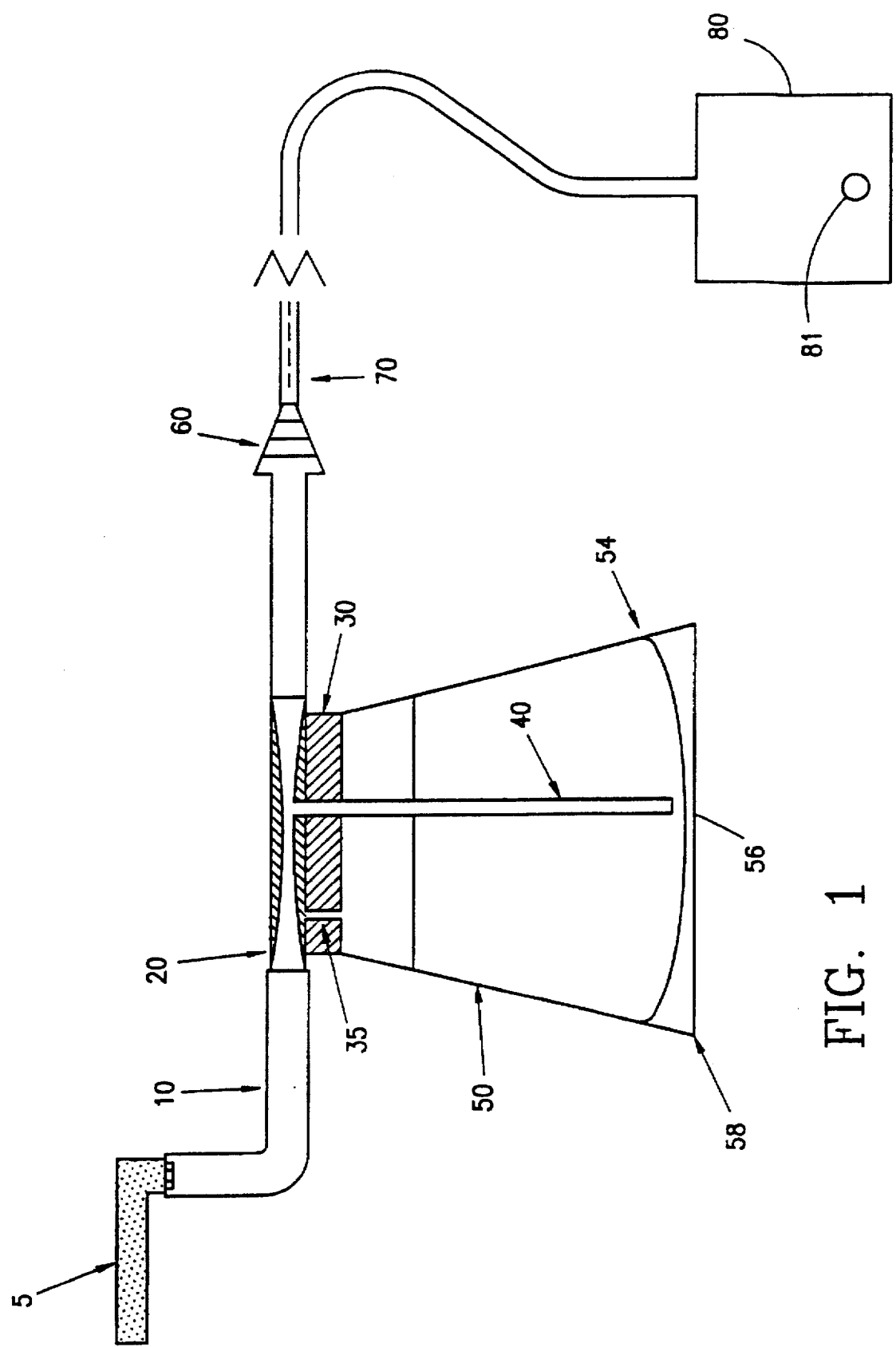
FIG. 1 depicts a pictorial representation of the present invention connected to the pressurized water source, secondary cleansing fluid container and the connection to night container tubing for filling, cleansing, and flushing.

FIG. 1 provides the overall pictorial representation of the present invention and is composed of a flexible intake tube, designated 10, providing connection to the interior water faucet, designated 5, for a source of the primary pressurized fluid water. The flexible intake tube 10 is connected at the opposite end to the proximal end of a venturi tube, designated 20, which is connected at the bottom edge to an interior threaded cap, designated 30, providing for a secure connection of a secondary cleansing fluid container, designated 50. The secondary fluid feed tube, designated 40, is attached to the venturi tube 20 near the distal end at a point providing negative pressure in the tube drawing the secondary fluid up into the tube by means of the negative pressure suction and providing the secondary fluid contact with intake faucet water for mixing at the outlet point in the venturi tube 20. The feed tube 40 draws the secondary fluid in at a point in the center of the concave internal base, designated 56, providing for minimal waste of the fluid. The threaded cap 30 has a vent hole, designated 35, to provide the secondary fluid at atmospheric pressure. The mixture of the primary fluid water mixed with the secondary cleansing and deodorizing fluid exits the distal end of the venturi tube 20 mixed together and flows into an adapter tip, designated 60 that fits securely and easily to the night urostomy container tubing, designated 70, of less than one half inch in diameter. The tip may be of various shapes and sizes depending on specific equipment requirements. The mixture of water and cleansing fluid is flushed into the night container 80 (not to scale) and then drained out 81.

The secondary cleansing and deodorizing fluid container, designated 50, comprises a threaded neck, designated 52, is approximately one half the diameter of the base, designated 58, and provides a secure attachment to the threaded cap, designated 30. The threaded design also allows for simple attachment and detachment of the fluid container for refilling purpose. The fluid container 50 is of a one stage conical design with the base 58 twice the size of the threaded neck 52 (not shown) providing a tip and spill resistance shape. The internal concave base, designated 54, is approximately one sixth the height of the fluid container 50 and provides for a place to draw the fluid into the feed tube, designated 40, at the center of the concave internal base, designated 56, providing for minimal fluid waste. This feature combined with the single stage conical design of the fluid container 50 gives the invention a large secondary cleansing fluid capacity.

Figure 2:
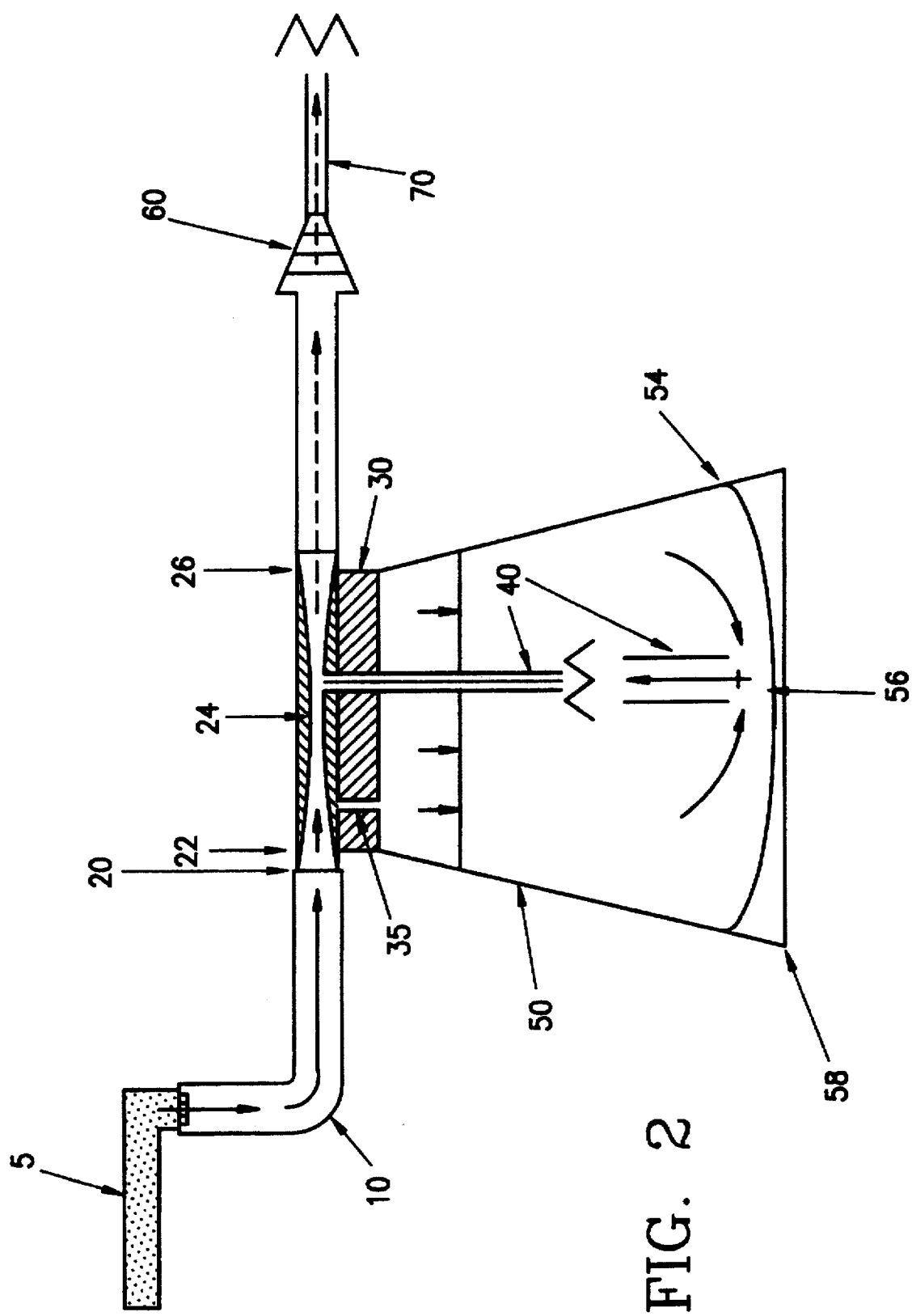
FIG. 2 depicts a schematic diagram of the fluid flow within the present invention.

FIG. 2 is a schematic diagram depicting the fluid flow within the present invention. The primary fluid source is the pressurized water at the faucet, designated 5, which flows through the flexible intake tube, designated 10, into the venturi designated 20. The purpose of the venturi 20 is to provide a tapered area starting at the venturi inlet, designated 22, that increases the pressure to a center point, designated 24, of minimal diameter and then tapering back to the inlet diameter at the distal end of the venturi tube outlet, designated 26. This configuration provides a negative pressure producing the suction at the secondary cleansing fluid feed tube exit point in the distal end of the venturi tube 20, producing mixing of the primary fluid water with the secondary cleansing fluid as the mixed fluid exits out the adapter tip, designated 60. The suction produced at the point where secondary feed tube 40 enters into the distal end of the venturi tube 20 draws the cleansing fluid in the cleansing fluid container, designated 50, at a center point, designated 56, of the concave internal base 58. The vent hole designated 35, in the threaded vent cap enables the top of the secondary cleansing fluid to remain at atmospheric pressure. The cleansing fluid flow is thereby always towards the concave center point 56 when the invention is maintained in the normal upright position and produces minimal waste of the secondary fluid when cleansing and flushing the urostomy night container.

Possible materials for the device may include, but should not be limited to, any plastic, hard rubber, glass, ceramic or composite that allows a rigid form; any metal that may be shaped either in a mold or through tooling, laser carving or other manner sufficient to produce the necessary form.

Possible methods of construction may include, but are not limited to, a single one piece molded venturi, cap and secondary fluid feed tube. The venturi may be an integral part of the cap or produced separately and attached through any reasonable method during the manufacturing process. The venturi tube, cap and feed tube or whole assembly may be produced in any part, section, split or division, including edifying the outer shape of the distal end of the venturi tube as an adapter tip to allow direct connection to the patients tubing, thereby removing the need for a tubing connection between said distal end and the adapter tip.

An additional method of construction would be to separate the venturi tube from the cap entirely and place it in-line in the water line. A flexible secondary fluid feed tube could then be used with any fluid container attaching to the in-line venturi and drawing the secondary fluid from said container. The only restriction being necessity to maintain atmospheric pressure on the surface of the secondary fluid in the container. In this case, a cap would not necessarily be required. Given this scenario, the apparatus could be used with any secondary fluid container including secondary fluid storage container (i.e., the bottle it came in). While this would function, it would not have the optimum advantage of tip resistance, as well as minimum secondary fluid waste.

CONCLUSION

A system and method has been shown in the above embodiments for the effective implementation of a urostomy patient irrigation system. While various preferred embodiments have been shown and described, it will be understood that there is no intent to limit the invention by such disclosure, but rather, it is intended to cover all modifications and alternate constructions falling within the spirit and scope of the invention as defined in the appended claims. The invention may also serve as an irrigation system for nasal-gastric tubes, colostomy patient equipment as well as many other surgical tubing applications. The invention should not be limited by size, materials or manufacturing methods. In addition, equivalent connectors and tubing structures may be substituted to perform similar functions.

What is claimed:

1. A waste equipment cleaning system for cleansing and deodorizing a medical container and associated tubing with a secondary cleansing fluid comprising:

a urostomy patient night drainage container, associated low pressure tubing and adapter;

a first connection of said adapter to a primary fluid pressurized water source;

a second connection of said adapter to a tip resistant secondary cleansing fluid container;

a venturi tube located within said adapter;

said secondary cleansing fluid container containing a secondary cleansing fluid and a secondary fluid feed tube operatively connected to said venturi tube;

an adapter tip connected to a distal end of said venturi tube for connection to said low pressure tubing, and wherein said primary fluid pressurized water source generates a suction within said venturi section to draw said secondary cleansing fluid from said secondary container to be mixed therewith and circulated throughout the urostomy patient night drainage container and associated tubing.

2. A waste equipment cleaning system as set forth in claim 1, wherein said venturi tube comprises two mirrored tapered conical sections designed such that the intake diameter is significantly larger than the midpoint tapered diameter, from which point then the distal conical section is tapered back to an outlet diameter, of the same diameter of the intake, providing a negative pressure at the distal portion of the tube when the pressurized water flows through the venturi tube.

3. A waste equipment cleaning system as set forth in claim 2, further comprising positioning of the feed tube towards the distal portion of the venturi tube for the negative pressure to provide suction for the secondary cleansing fluid which will then be in fluid contact with the pressurized primary water fluid for mixing in a fluid space between the secondary fluid feed tube intake and the distal end of the venturi tube.

4. A waste equipment cleaning system as set forth in claim 1, wherein said adapter comprises a tapered design for connection to said medical container tubing of less than one half an inch in diameter.

5. A waste equipment cleaning system as set forth in claim 1, wherein said operative connection to said secondary cleansing fluid container comprises a threaded cap which receives said secondary cleansing fluid tube and is further vented.

6. A waste equipment cleaning system as set forth in claim 5, wherein said vented cap comprises a vent hole for the secondary cleansing fluid in the container to be maintained at atmospheric pressure for a proper draw into the secondary cleansing fluid feed tube intake.

7. A waste equipment cleaning system as set forth in claim 1, wherein said secondary fluid container comprises a single stage conical container with a base twice the diameter of the neck thereby providing a large fluid capacity that is tip and spill resistant.

8. A waste equipment cleaning system as set forth in claim 1, wherein said secondary fluid container comprises a concave internal base constructed about one sixth the height to provide a continuous feed to a center concave point thereby providing for minimal waste of the secondary cleansing fluid.

9. A urostomy patient equipment system for cleansing and deodorizing a urostomy container and tubing with a secondary cleansing fluid comprising:

- a urostomy patient night drainage container, associated low pressure tubing and adapter;
- a first connection to a primary fluid pressurized water source;
- a venturi tube operatively connected to said first connection;
- a tip resistant secondary cleansing fluid container and secondary fluid feed tube operatively connected to venturi tube;
- an adapter tip connected to a distal end of said venturi tube for connection to urostomy container tubing, and
- wherein said primary fluid pressurized water source generates a suction within said venturi section to draw said secondary cleansing fluid from said secondary container to be mixed therewith and circulated throughout the urostomy patient night drainage container and associated tubing.

10. A urostomy patient equipment system as set forth in claim 9, wherein said venturi tube comprises two mirrored tapered conical sections designed such that the intake diameter is significantly larger than the midpoint tapered diameter, from which point then the distal conical section is tapered back to an outlet diameter, of the same diameter of the intake, providing a negative pressure at the distal portion of the tube when the pressurized water flows through the venturi tube.

11. A urostomy patient equipment system as set forth in claim 10, further comprising positioning of the feed tube towards the distal portion of the venturi tube for the negative pressure to provide suction for the secondary cleansing fluid which will then be in fluid contact with the pressurized primary water fluid for mixing in a fluid space between the secondary fluid feed tube intake and the distal end of the venturi tube.

12. A urostomy patient equipment system as set forth in claim 9, wherein said adapter comprises a tapered design for connection to said urostomy container tubing of less than one half an inch in diameter.

13. A Urostomy patient equipment system as set forth in claim 9, wherein said operative connection to said secondary cleansing fluid container comprises a threaded cap which receives said secondary cleansing fluid tube and is further vented.

14. A urostomy patient equipment system as set forth in claim 13, wherein said vented cap comprises a vent hole for the secondary cleansing fluid in the container to be maintained at atmospheric pressure for a proper draw into the secondary cleansing fluid feed tube intake.

15. A urostomy patient equipment system as set forth in claim 9, wherein said secondary fluid container comprises a single stage conical container with a base twice the diameter of the neck thereby providing a large fluid capacity that is tip and spill resistant.

16. A urostomy patient equipment system as set forth in claim 9, wherein said secondary fluid container comprises a concave internal base constructed about one sixth the height to provide a continuous feed to a center concave point thereby providing for minimal waste of the secondary cleansing fluid.

* * * * *